(12) United States Patent
Duan et al.

(10) Patent No.: US 10,779,709 B2
(45) Date of Patent: Sep. 22, 2020

(54) SYSTEM AND METHOD FOR USING A CAPSULE DEVICE

(71) Applicant: Ankon Medical Technologies (Shanghai) Co., LTD., Shanghai (CN)

(72) Inventors: Xiaodong Duan, Pleasanton, CA (US); Shaobang Zhang, Hangzhou (CN)

(73) Assignee: Ankon Medical Technologies (Shanghai) Co., LTD, Shanghai (CN)

( * ) Notice: Subject to any disclaimer, the term of this patent is extended or adjusted under 35 U.S.C. 154(b) by 0 days.

(21) Appl. No.: 16/459,438

(22) Filed: Jul. 1, 2019

(65) Prior Publication Data

US 2019/0320884 A1    Oct. 24, 2019

Related U.S. Application Data

(62) Division of application No. 15/274,845, filed on Sep. 23, 2016, now Pat. No. 10,478,048.

(51) Int. Cl.
| | |
|---|---|
| *A61B 1/00* | (2006.01) |
| *A61B 34/00* | (2016.01) |
| *A61B 5/00* | (2006.01) |
| *A61B 5/06* | (2006.01) |
| *A61B 1/04* | (2006.01) |

(52) U.S. Cl.
CPC .......... *A61B 1/00158* (2013.01); *A61B 1/041* (2013.01); *A61B 5/062* (2013.01); *A61B 5/6861* (2013.01); *A61B 34/73* (2016.02); *A61B 2034/732* (2016.02)

(58) Field of Classification Search
None
See application file for complete search history.

(56) References Cited

U.S. PATENT DOCUMENTS

| | | | |
|---|---|---|---|
| 2005/0256398 A1* | 11/2005 | Hastings | A61B 34/73 600/423 |
| 2008/0300458 A1* | 12/2008 | Kim | A61B 1/00158 600/118 |
| 2013/0267788 A1* | 10/2013 | Duan | B25J 11/00 600/300 |
| 2013/0303847 A1* | 11/2013 | Sitti | A61B 1/00158 600/104 |
| 2014/0148643 A1 | 5/2014 | Kawano | |
| 2015/0018614 A1* | 1/2015 | Duan | A61B 1/00006 600/109 |

FOREIGN PATENT DOCUMENTS

| | | | | |
|---|---|---|---|---|
| CN | 103169443 A1 | 6/2013 | | |
| KR | 20040108277 A | * 12/2004 | | A61B 1/00 |
| WO | 2009107892 A1 | 9/2009 | | |

\* cited by examiner

*Primary Examiner* — Aaron B Fairchild
(74) *Attorney, Agent, or Firm* — Treasure IP Group, LLC

(57) ABSTRACT

The present invention discloses a system to control a movement of a magnetic capsule using an external magnet control system. The external magnet control system includes more than one external magnetic balls, and at least one external magnetic ball can be moved freely in five degrees of the freedom.

7 Claims, 20 Drawing Sheets

FIG. 21   FIG. 22   FIG. 23   FIG. 24
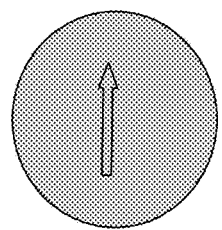 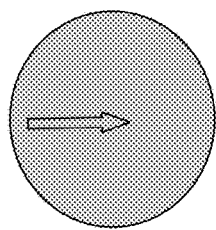 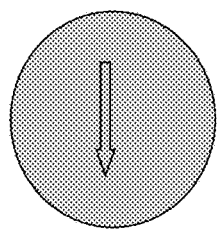 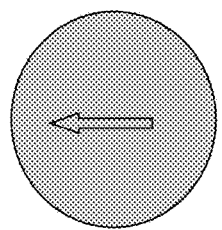
 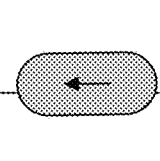  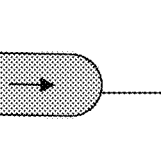
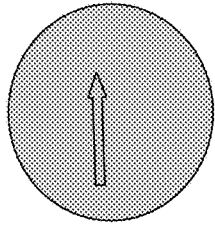 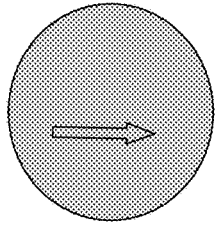 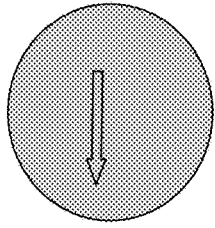 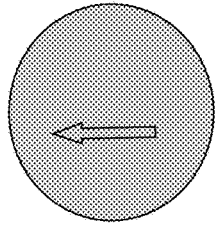

FIG. 29

| | |
|---|---|
| patient lays down the examing bed, the capsule is inside the colon. | move the two magnetic balls directions so that the capsule is imaging the open space (tube hole) of colon. and move the balls to be ahead of the capsule's moving direction. |
| two magnetic balls vertical aligned and have horizontal magnetization. And the distance between the two balls' centers are relatively far (~60cm) | to move the capsule forward rotate the two magnetic balls' magnetization as in Fig.1(a); to move the capsule backward rotate the two magnetic balls' magnetization as in Fig.1(b); |
| moving two magnetic balls together in XY plane to find a relative larger magnetic fields measured by the magnetic sensors inside the capsules | move the two magnetic balls close to each other at the same velocity to near the patient's body surface but not touch the patient for the safe reason. The capsule will move toward the line between the magnetic balls' centers. |
| through two three dimentional magnetic sensors and one three dimentional acceleration sensor inside the capsules, the position and orientation of the capsule can be calculated, and adjust the two balls so that the capsule is in the mid of two balls | adjust the two balls' XY plane location so that the capsule will move along the colon by the guidance of two magnetic balls. The same method can be used for the small bowl. |

SYSTEM AND METHOD FOR USING A CAPSULE DEVICE

CROSS-REFERENCE

This application is related to the co-pending application U.S. Ser. No. 15/274,771, filed on Sep. 23, 2016. This application is a divisional application of Ser. No. 15/274,845, filed on Sep. 23, 2016.

TECHNICAL FIELD OF THE DISCLOSURE

This patent application relates to the art of capsule devices to be used in medical related applications, and more particularly, to systems which use two external magnetic generating means to navigate a magnetic capsule through a patient's GI tract and methods of using the same.

BACKGROUND OF THE DISCLOSURE

The magnetic controllable capsule endoscope has been widely used commercially in the stomach examination and been proven to be very successful. However, the magnetically controllable capsule endoscope is not currently adapted to be placed inside a small bowel and colon to perform a routine examination.

To date, there are three types of external magnetic field generation systems to guide a magnetic capsule endoscope while traveling in a patient's GI tract. They are electromagnetic coils, electromagnet, and permanent magnet. In order to meet the requirement of providing sufficient driving force, by external magnetic field or external magnetic gradient, for the purpose of moving a typical magnetic capsule endoscope throughout a patient's small bowel, if electromagnetic coils and electromagnet systems are used, the power consumption of these two systems must be significant, and heat dissipation can make these two systems even more bulkier and eventually very expensive to be built and operated. Additionally, for electromagnetic coils and electromagnet systems, achieving proper electromagnetic compatibility (EMC) is also a big challenge, and potential safety issue relating to the electromagnetic field also exists.

Comparing with electromagnetic coils, the permanent magnet is a much more clean and efficient way to generate strong magnetic field or field gradient. However, the control algorithm for the permanent magnet is much more complex than that of the electromagnetic coils. The electromagnet has more flexibility then the permanent magnet, since its magnetic strength can be adjusted by the electrical current. However, for the control of the movement of the magnetic capsule, the electromagnet has the same order of the complexity of the permanent magnetic field. And to achieve the same magnetic field strength or field gradient, the electromagnet will need to take 2-3 times larger space than that of the permanent magnet. As for the permanent magnet, a sphere shape is the most efficient shape for remote magnetic field or field gradient generation.

Therefore, when a magnetic control system to navigate a capsule through a small bowel is needed, the system should employ an external permanent magnet dipole as the external control system and it is easy to use.

SUMMARY OF THE INVENTION

The present invention discloses a system and method that can be used to examine a patient's GI tract.

It is one object of the present invention to invent a system that can use permanent magnet to control a movement of a magnetic capsule placed in vivo.

It is another object of the present invention that the magnetic capsule can be moved in three dimensions freely, having 5 degrees of the freedom.

It is another object of the present invention that the magnetic capsule can move and adjust orientation by the external magnet.

In one aspect of the present invention, a system for controlling movement of a magnetic capsule in a human GI tract, is described. The system comprises a magnetic dipole for placement in a human GI tract, an external magnet control system, having more than five degrees of freedom, that can apply external translational and/or rotational magnetic field force to the magnetic capsule; and the magnetic dipole is enclosed in a capsule, said capsule is having a length. Wherein the orientation of magnetic dipole is parallel to the length of the capsule. Further, the system includes more than one external magnetic balls, and at least one external magnetic ball can be moved freely in five degrees of the freedom.

In a second aspect of the present invention, a mechanical control of the system is described. The system comprises two magnetic balls, each is controlled by their respective individual movement control assembly, which can be operated either simultaneously or separately.

The system comprises a first external magnetic control assembly and a second external magnetic control assembly. Each external magnetic control assembly comprises a magnetic field generation means, two horizontal translation means, one vertical translation means, horizontal rotating means and vertical rotation means.

In a third aspect of the present invention, an apparatus for medical examination is described. The medical apparatus for examining a patient's GI tract, comprises a base, situated on a ground, a pair of vertical supporting frame assemblies, two spherical shaped external magnets, each spherical shaped external magnet attached to a movement control assembly, wherein both spherical shaped external magnets are used to navigate a magnetic capsule placed inside the patient along its progressive pathway.

In a fourth aspect of the present invention, a method for controlling movement of a magnetic capsule in a human GI tract, wherein said method comprises preparing a patient laying down on the examination bed, when the capsule is inside the patient;

aligning two magnetic balls vertically where both have horizontal magnetization;

positioning the two magnetic balls so that a distance between centers of the two magnetic balls is more than 50 cm in the vertical direction;

moving the two magnetic balls simultaneously in a XY plane;

measuring the resulting combined magnetic field by using magnetic sensors inside the capsules;

calculating a position and orientation of the magnetic capsule by two three dimensional magnetic sensors and one three dimensional acceleration sensor inside the capsule;

adjusting the vertical and horizontal position of the two magnetic balls so that the capsule is between the two balls;

moving the two magnetic balls to adjust their magnetic directions so that the magnetic capsule can image an open space of the colon; and moving the two magnetic balls to be ahead of the capsule's moving direction;

moving the magnetic capsule forward by rotating the two magnetic balls to change their magnetization direction.

BRIEF DESCRIPTION OF THE DRAWINGS

Exemplary embodiments of the disclosure will be more clearly understood from the following detailed description taken in conjunction with the accompanying drawings in which:

FIGS. 21-24 are schematic illustration of how to rotate a magnetic capsule in xz plane;

FIG. 29 is a process flow diagram to show how the system is used.

DETAILED DESCRIPTION OF SELECTED EXAMPLES

Figure 1:
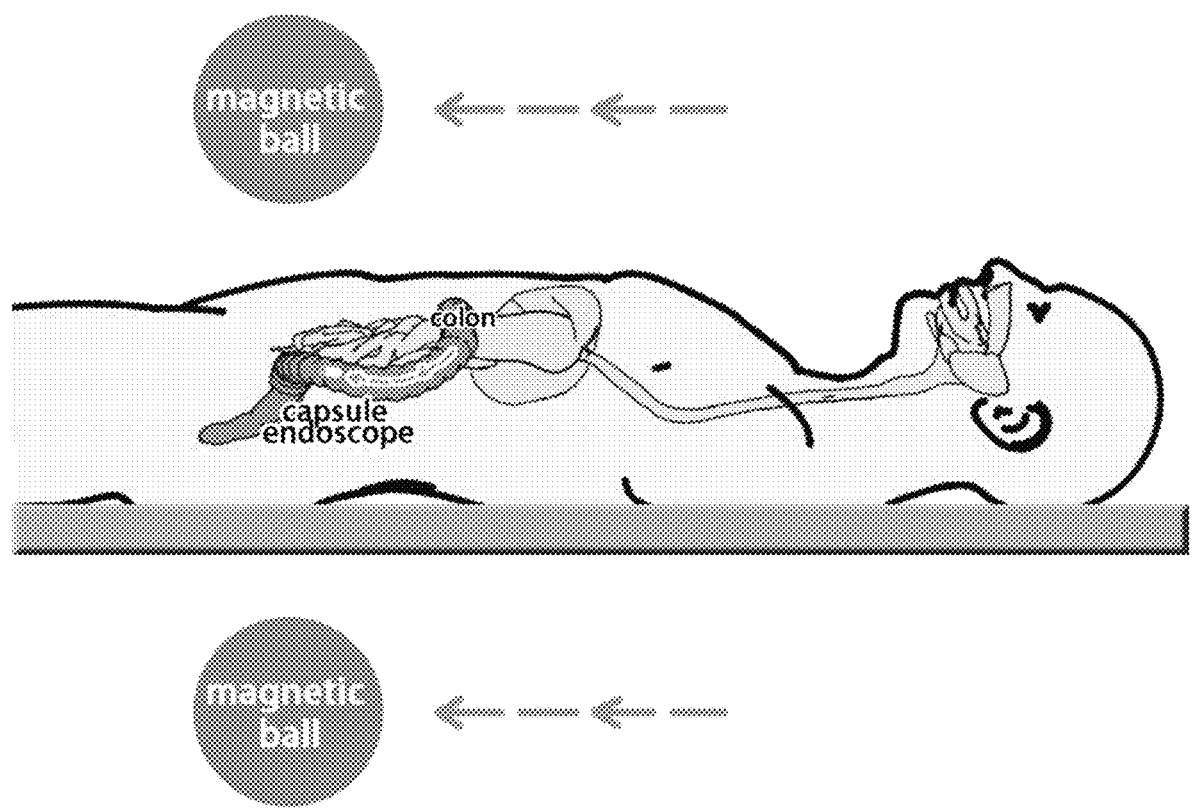
FIG. 1 shows a schematic illustration of a magnetic capsule system in accordance with aspects of the present invention.

Hereinafter, selected examples of a magnetic capsule system to be placed in a target location and its external control system, and methods of using the same will be described in detail with reference to the accompanying drawings. For purpose of simplicity, the magnetic capsule and its external system is explained in the context of biomedical applications, i.e. the target location is an in vivo location, for example, a location inside a digestive tract. For purpose of simplicity, the medical device disclosed herein is designed to be placed in vivo. One of the non-invasive methods of delivery is by to swallow the magnetic capsule into a digestive tract. Therefore, the medical device disclose herein is referred as a capsule, which should not be construed as a limitation for its shape, dimension or size. The capsule device disclosed herein and methods of using the same can be implemented for many other applications as long as there is a movement of the magnetic capsule in the target location, which needs to be controlled externally from one location to another location.

In the scope of the present invention, xyz coordinate system is used to define a position or direction. FIG. 3 shows xyz axis direction with respect to the orientation of the medical system in the scope of the present invention. It is for illustration purposes only. It should not be construed as a limitation. For example, according to FIG. 3, in referring to FIG. 2, x direction is the direction the bed moves, which is from back to forward; y direction is the direction from one supporting frame to another opposing supporting frame, which is from left to right, and z direction is the direction to move the magnets closer and away to the patient, which is the up down direction. Horizontal rotation means a rotation around z axis, along xy plane, for example rotation from left to right, when viewing from the front of the apparatus. Vertical rotation means a rotation around y axis, along yz plane, for example, rotation from top to bottom, when viewing from the front of the apparatus.

Elements in the figures are listed below.
1. Motor 1
2. Z-axis upper assembly 1
3. Y-axis upper horizontal assembly
4. Motor 3
5. Magnetic ball 1
6. Right supporting frame assembly
7. Right sliding rail for the bed
8. Magnetic ball 2
9. Y-axis lower horizontal assembly
10. Motor 8
11. Z-axis uplift assembly 2
12. Motor 6
13. Base
14. Motor 2
15. Motor 4
16. Motor 5
17. Left supporting frame assembly
18. Bed
19. Left sliding rail for the bed
20. Motor 9
21. Motor 10
22. Motor 7

Details of the elements and their functions are summarized below.
1. Motor 1:
provide power to move the upper magnetic ball up in Z direction
2. Z-axis upper assembly 1
movement control parts for the upper magnetic ball along Z-axis are all placed on Z-axis upper assembly
3. Y-axis upper horizontal assembly
movement control parts for the upper magnetic ball along Y-axis are all placed on Y-axis upper assembly
4. Motor 3
provide power to move the upper magnetic ball up in x direction
5. Magnetic ball 1
the magnetic ball above the bed
6. Right supporting frame assembly
supporting frame on the right and parts attached to it
7. Right sliding rail for the bed
sliding rail for the bed on the right side
8. Magnetic ball 2
the magnetic ball below the bed
9. Y-axis lower horizontal assembly
movement control parts for the lower magnetic ball along Y-axis are all placed on Y-axis lower assembly
10. Motor 8
provide power to move the lower magnetic ball in x direction
11. Z-axis uplift assembly 2
movement control parts for the lower magnetic ball along z-axis are all placed on z-axis lower assembly
12. Motor 6
provide power to move the lower magnetic ball in z direction
13. Base
apparatus base, placed on the ground
14. Motor 2
provide power to move the upper magnetic ball in y direction
15. Motor 4
provide power to turn the upper magnetic ball along the horizontal plane, rotate around the z direction
16. Motor 5
provide power to turn the upper magnetic ball along the vertical plane, rotate around the z direction
17. Left supporting frame assembly
Left apparatus supporting frame
18. Bed
Bed to provide support to a patient and carry the patient into/out of the examination area
19. Left sliding rail for the bed
sliding rail for the bed on the left
20. Motor 9
provide power to rotate the lower magnetic ball along the vertical plane, rotate around the z direction
21. Motor 10
provide power to rotate the lower magnetic ball along the horizontal plane, rotate around the z direction
22. Motor 7
provide power to move the lower magnetic ball in the y direction The present invention discloses a system uses to examine GI tract of a patient, especially small bowl. The system uses magnetic capsule. The magnetic capsule comprises a permanent magnet, which respond to an external magnetic control system. The present invention discloses a system utilizes more than one external magnet to control the movement of the magnetic capsule.

Two Magnets

Referring to FIG. 1, the magnetic capsule of the present invention is meant to be used for a patient's GI tract examination, in particular for small bowl. The magnetic capsule further comprises an imaging means, which can examine the interior of the GI tract of the patient. In the present invention, the magnet capsule moves in the small bowl because of the combined magnetic field generated by both external magnets.

Figure 9:
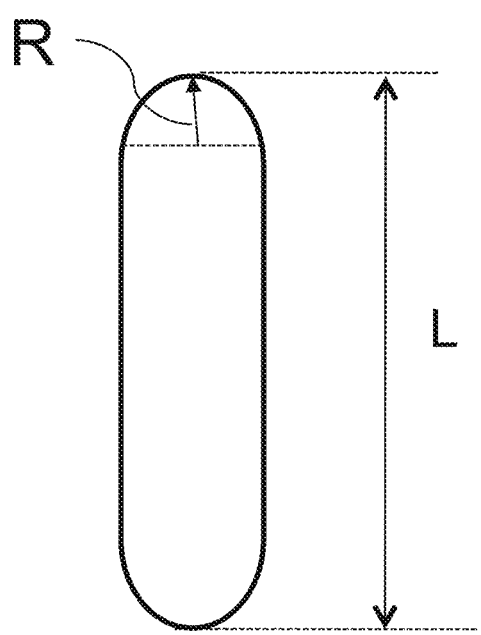
FIG. 9 is an illustration of a magnetic capsule in the accordance with the aspect of the present invention.

In the present invention, the magnetic capsule can be of any shape. One exemplary magnetic capsule is schematically illustrated in FIG. 9, the capsule has a length L. A permanent magnetic dipole is enclosed in the housing. In one example, the length of the capsule is parallel to the magnetization direction (N→S) of the capsule. In another example, the length of the capsule is perpendicular to the magnetization direction (N→S) of the capsule. In the operation embodiments depicted in figures of the present invention, the magnetization direction (N→S) of the capsule is parallel to the length of the magnetic capsule. Herein, length is directed to describe a longest dimension of the capsule. Because it is desired to have the longest dimension of the capsule parallel to the interior wall of the small bowel to reduce discomfort.

In the present invention, it is disclosed a system comprises two magnetic generation means. Each magnetic generation means comprises an external magnetic control assembly. The external magnetic control assembly provides power to move the magnetic generation means' position and magnetization direction with respect to the patient, in order to provides optimal magnetic field guidance to the magnet capsule.

In one embodiment of the present invention, two magnetic generation means each has a permanent magnetic dipole. In example, the two magnetic generation means have equal magnitudes of magnetic dipoles. In the scope of the present invention, equal magnitudes means, one magnetic dipole is at 95%-105% of the other magnetic dipole.

In one embodiment of the present invention, each of the two magnetic generation means is spherical shaped. In one example, both magnetic balls have the same diameter. Each magnetic ball has a weight center and a magnetization center. In one example, the magnetization center for both spherical shaped magnetic generation means is always aligned in one of the three coordinates (x, y, z) direction. In another example, the weight center and magnetization center coincide with each other. In still another example, the weight center for each spherical shaped magnetic generation means is always aligned in two of the three coordinates (x, y, z) direction. For instance, referring to FIGS. 4-8, the two magnetic balls are the in the same xy position and only differ in the vertical z direction.

The purpose of the present invention is to provide a better external magnetic control to the magnetic capsule during a small bowel examination. Therefore, more than one magnet is used to provide a distributed external magnetic field, which is not able to achieve by using one single magnet and one magnetic field. The two magnets are always on and off at the same time during the patient examination period.

Therefore, it is desired to place the patient in between the two external magnets. After the magnetic capsule has been introduced into the patient, the patient is ready for GI tract examination, the patient is invited to enter the medical apparatus.

In one embodiment of the present invention, the two magnetic generation means are placed above and below the patient, when the patient lies down on a platform or bed in the medical examination system.

In another embodiment of the present invention, the two magnetic generation means are placed in the front or behind the patient, when the patient stands in in the space of the medical examination system. In still another embodiment of the present invention, the two magnetic generation means are placed on the left and right of the patient, when the patient stands in the space of the medical examination system. In all the above embodiments, for safety and other reasons, the magnetic ball is positioned at least 5-25 cm away from a surface of the patient.

In the scope of the present invention, in the embodiment of two magnetic generations means are placed above and below the patient, when the patient lies down on a platform or bed in the medical examination system, referring to FIGS. 3 and 4, the x direction is a front-back direction; y direction is the left-right direction; and z direction is vertical up-down direction; horizontal rotation is rotation along yz plane, rotation around y axis; and vertical spinning is rotation along xy plane, rotation around z axis.

In the embodiment of two magnetic generations means are placed in front of and behind the patient, when the patient stands in the middle of the open medical examination area with the semi-enclosed system, the x direction is a front-back direction; z direction is the left-right direction; and y direction is vertical up-down direction; horizontal rotation is rotation along yz plane, rotation around z axis; and vertical spinning is rotation along xz plane, rotation around y axis.

In the scope of the present invention, any system that can generate a magnetic field can be used as magnetic generation means. In one embodiment, any materials that have permanent magnetic dipole can be used as external magnetic means. The materials are of the external magnetic balls are selected from Fe, Co or Ir and any alloy from them. In one example, the two magnetic balls are made of the same magnetic materials.

In the scope of the present invention, the external magnets can be of any shape. The spherical shape is preferred because spherical shaped magnetic is known to generate a less complicated magnetic field. The two external magnets can be at different sizes according to the scope of the present invention.

In a preferred example, the two external magnets are made of the same material composition; it is preferred to provide the two external magnets with same sizes, so that the operations are more intuitive and easier to operate. When two external magnets provide the magnetic fields at the similar strength, the operator can easily make the magnet closer or further away from the patient in order to make the associated magnetic field stronger or weaker.

The two external magnets are the same size means one external magnet is having a size or volume at about 95%-105% of the other external magnet.

In a preferred example, the two external magnets are made of the same material composition; it is preferred to provide the two external magnets with same weight, so that the operations are more intuitive and easier to operate.

The two external magnets are the same weight means one external magnet is having a size or volume at about 95%-105% of the other external magnet.

In the event that the two external magnets have different weight, or size, which can be taken into the consideration when setting up the operation system and movement protocols. For example, if one magnet is bigger than the other, the bigger magnet can be positioned at a distance farther away from the patient than the smaller magnet.

In generally, the magnets are made of Aluminum, Iron Boron alloy.

By doing so, the magnets can be moved gently and smoothly to guide the movement of the magnetic capsule so that the examination can be finished within a reasonable amount of the time, the amount date to be collected are enough for the doctors to evaluate and yet the patient does not suffer much discomfort due the movement magnetic capsule.

Two Magnetic Movement Control Assembly

Each external magnet is attached to an external magnet movement control assembly. Each external magnet movement control assembly has motors and arms that moves the magnet in more than 3 degrees of freedoms.

Each magnetic control assembly can be operated individually. Each magnetic generation means can move along x direction, y direction, z direction, and further rotate horizontally and vertically. In another words, each magnetic generation means can move in 5 degrees of freedom. Each external control assembly can provide power for movement individually in the five degrees of freedom.

Referring to FIGS. 5-8, each magnetic generation means have five motors to provide the power for movement in each degree of freedom. Totally, there are 10 motors. Each motor is connected to a driver, which can be controlled directly.

In one embodiment of the present invention, the two magnetic generation means moving along the same direction can be controlled simultaneously. In one example, the two magnets move horizontally in either x, y direction simultaneously.

In accordance with the aspect of the present invention, in one embodiment, the system for navigating a magnetic capsule inside a patient, comprises more than one magnetic field generation means and more than one external movement control assemblies. In the present invention, the system comprises a first magnetic field generation means, positioned on a first side of the patient, configured to provide a first magnetic field to move the magnetic capsule; and a first external movement control assembly, comprise a first horizontal translation means, which can move the first magnetic field generation means along an x-axis direction;

a second horizontal translation means, which can move the first magnetic field generation means along a y-axis direction;
a first vertical movement means, which can move the first magnetic field generation means along a z-axis direction;
a first rotation means, which can turn the first magnetic dipole along or parallel to a xy plane defined by the x-axis and y-axis, or rotate around the z-axis direction;
a second rotation means which can turn the first magnetic dipole around the x-axis direction;
wherein the can each adjust the position and orientation of the first magnetic field generation means individually.

The system further includes a second external magnetic control assembly, directed to control the movement of the second magnetic field generation means, which is positioned on a second side of the patient, configured to provide a second magnetic field to move the magnetic capsule.

The second external magnetic control assembly comprises, in one example, a third horizontal translation means which can move the second magnetic field generation means along the x-axis direction.

In another example, the second external magnetic control assembly further comprises, a fourth horizontal translation means which can move the second magnetic field generation means along the y-axis direction.

In another example, the second external magnetic control assembly further comprises, a second vertical movement means which can move the first magnetic field generation means along the z-axis direction.

In another example, the second external magnetic control assembly further comprises, a third rotation means which can turn the second magnetic dipole along or parallel to the xy plane defined by the x-axis and y-axis, or rotate around the z-axis direction.

In another example, the second external magnetic control assembly further comprises, a fourth rotation means which can turn the second magnetic dipole around the x-axis direction.

In the second external magnetic control assembly, wherein each translation means and rotation means can adjust the position and orientation of the first magnetic field generation means individually.

Further, the first and external magnetic control assembly can operate sequentially or simultaneously including at least one movement means.

In one embodiment, the first and second magnets are above and below the patient having a magnetic capsule inside patient's GI tract. In one example, the first horizontal translation means for the first magnetic field generation means and the third horizontal translation means for the second magnetic field generation means can be moved together.

In another example of the same embodiment, the second horizontal translation means for the first magnetic field generation means and the fourth horizontal translation means for the second magnetic field generation means can be moved together.

In another example of the same embodiment the first vertical translation means for the first magnetic field generation means and the second vertical translation means for the second magnetic field generation means can be moved together.

In still another example of the same embodiment the first rotation means for the first magnetic field generation means and the third rotation means for the second magnetic field generation means can be moved together.

In yet another example of the same embodiment, the second rotation means for the first magnetic field generation means and the fourth rotation means for the second magnetic field generation means can be moved together.

Figure 13:
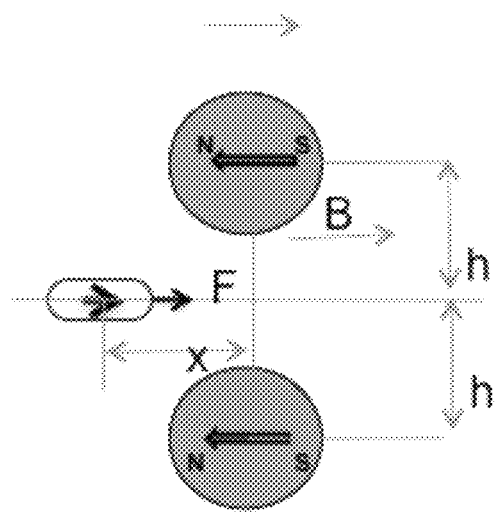
FIG. 13 is a schematic illustration of another operation condition wherein the magnetizations of the two magnets are opposite to the magnet capsule.
Figure 14:
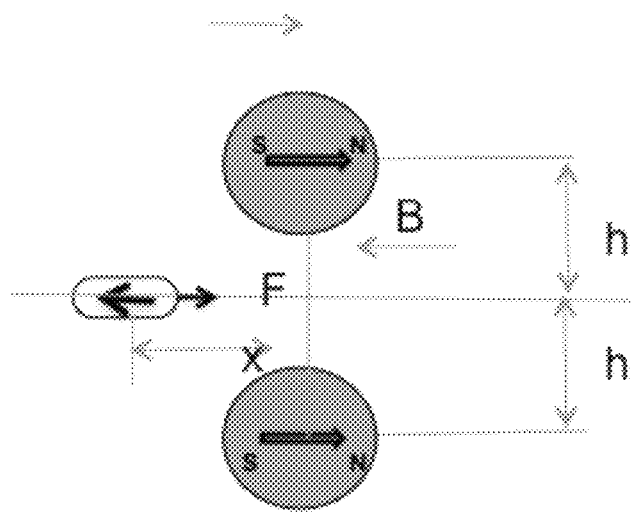
FIG. 14 is a force and magnetic field relative distribution chart when the positions of the two magnets and magnetic capsule are as listed in FIG. 13.
Figure 15:
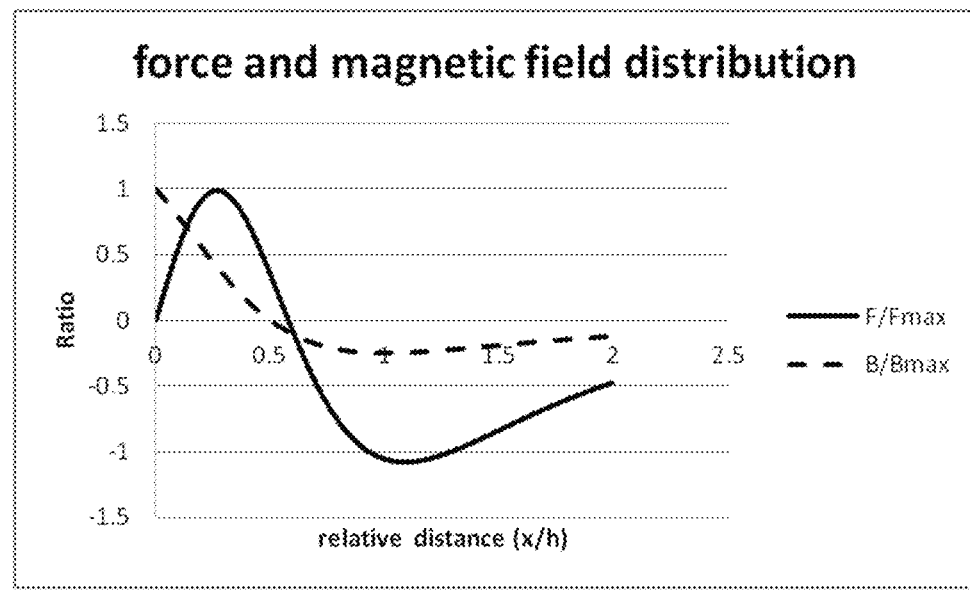
FIG. 15 is schematic illustration of another operation condition wherein two magnetic balls are aligned vertically, and their magnetizations of both balls are same and the magnetization directions are mirror image to each other along the middle plane between them.
Figure 16:
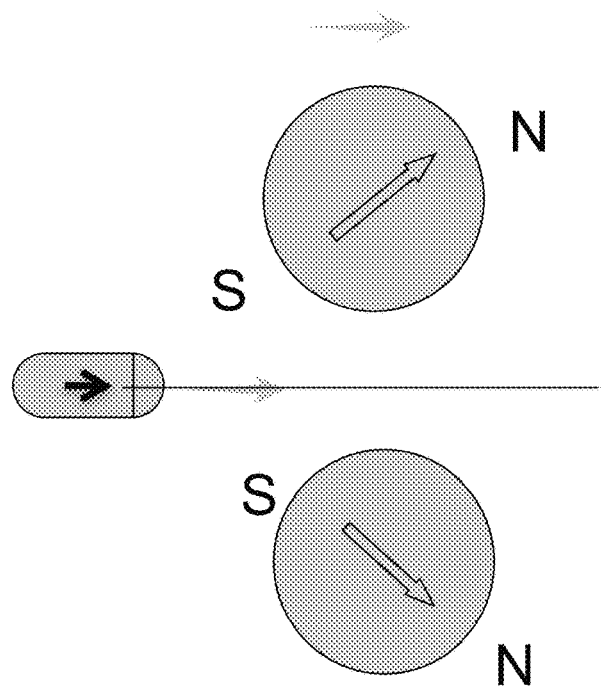
FIG. 16 is schematic illustration of another operation condition wherein two magnetic balls are aligned vertically, their magnetizations of both balls are same and the magnetization directions are mirror image to each other along the middle plane between them, and wherein the magnetic capsule is dragged forward.
Figure 17:
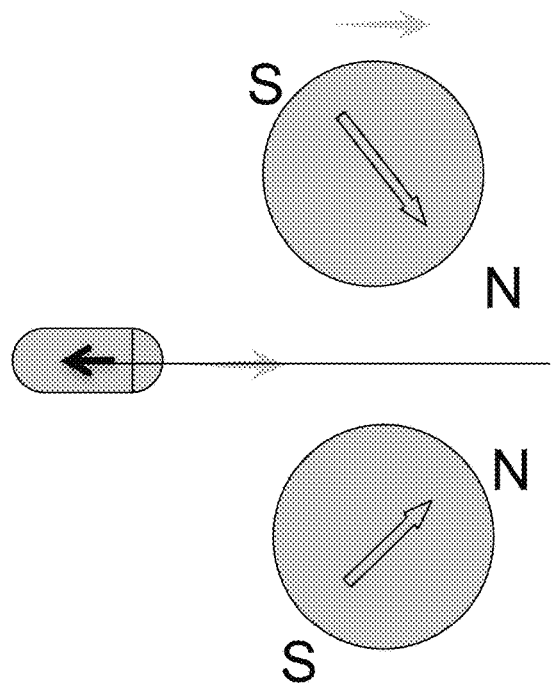
FIG. 17 is schematic illustration of another operation condition wherein two magnetic balls are aligned vertically, their magnetizations of both balls are same and the magnetization directions are mirror image to each other along the middle plane between them, and wherein the magnetic capsule is dragged forward.
Figures 18A, 19:
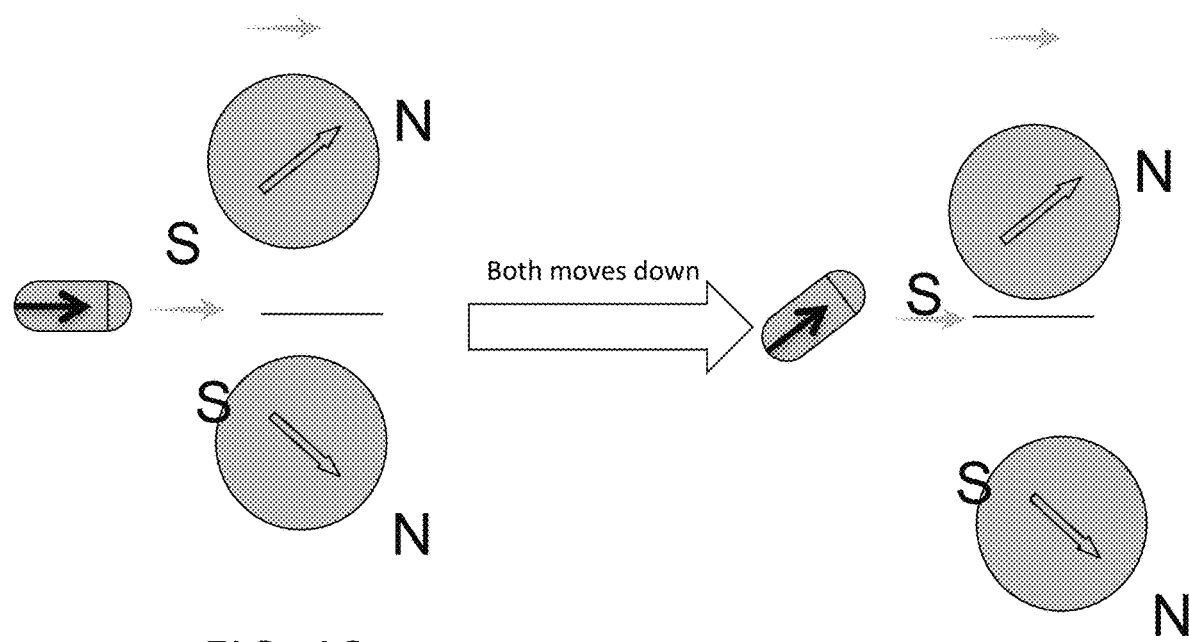
FIGS. 18a and 18b are same figure illustrating initial positions and orientations of the magnetic capsule and external magnetic balls in a process to change a magnetic capsule through the adjustment in the external magnetic system.
FIG. 19 is a finished position and orientation of the magnetic capsule and external magnetic balls in a process to change a magnetic capsule through the adjustment in the external magnetic system.
Figures 18B, 20:
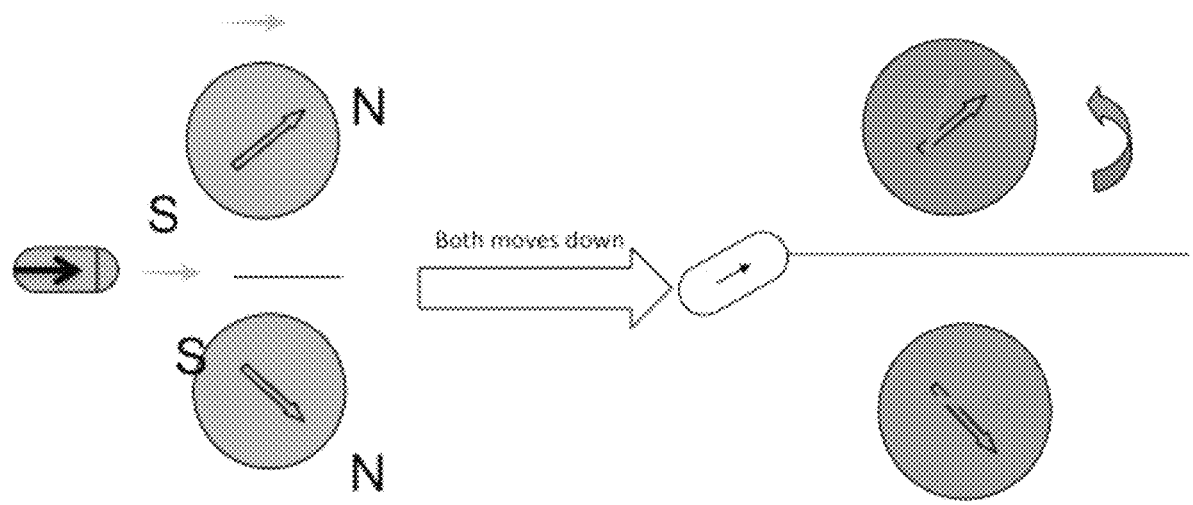
FIG. 20 is another finished position and orientation of the magnetic capsule and external magnetic balls in an alternative process to change a magnetic capsule through the adjustment in the external magnetic system.
Figure 25:
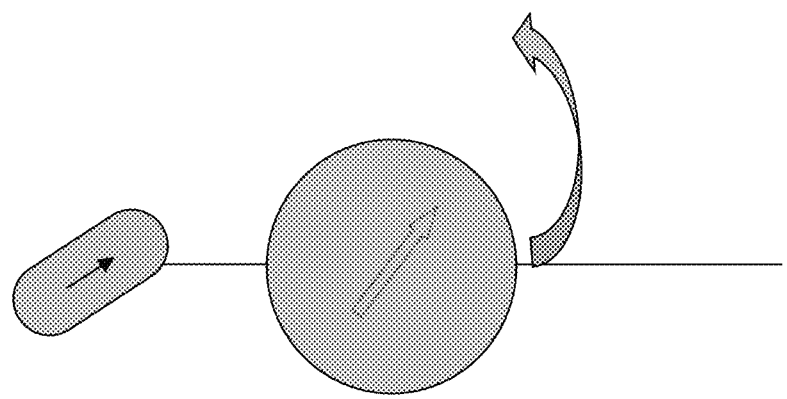
FIG. 25 is a top view of a schematic illustration of how to rotate a magnetic capsule in xy plane.
Figure 26:
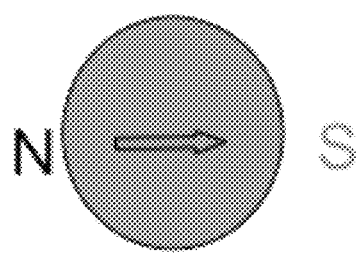
FIG. 26 shows a side view of a schematic diagram to how to spin a magnetic capsule in xy plane.
Figure 26:
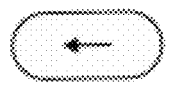
Figure 26:
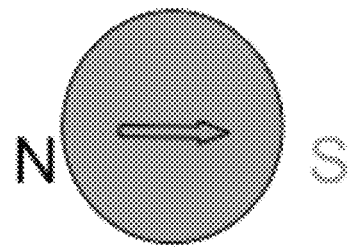
Figures 27, 28:
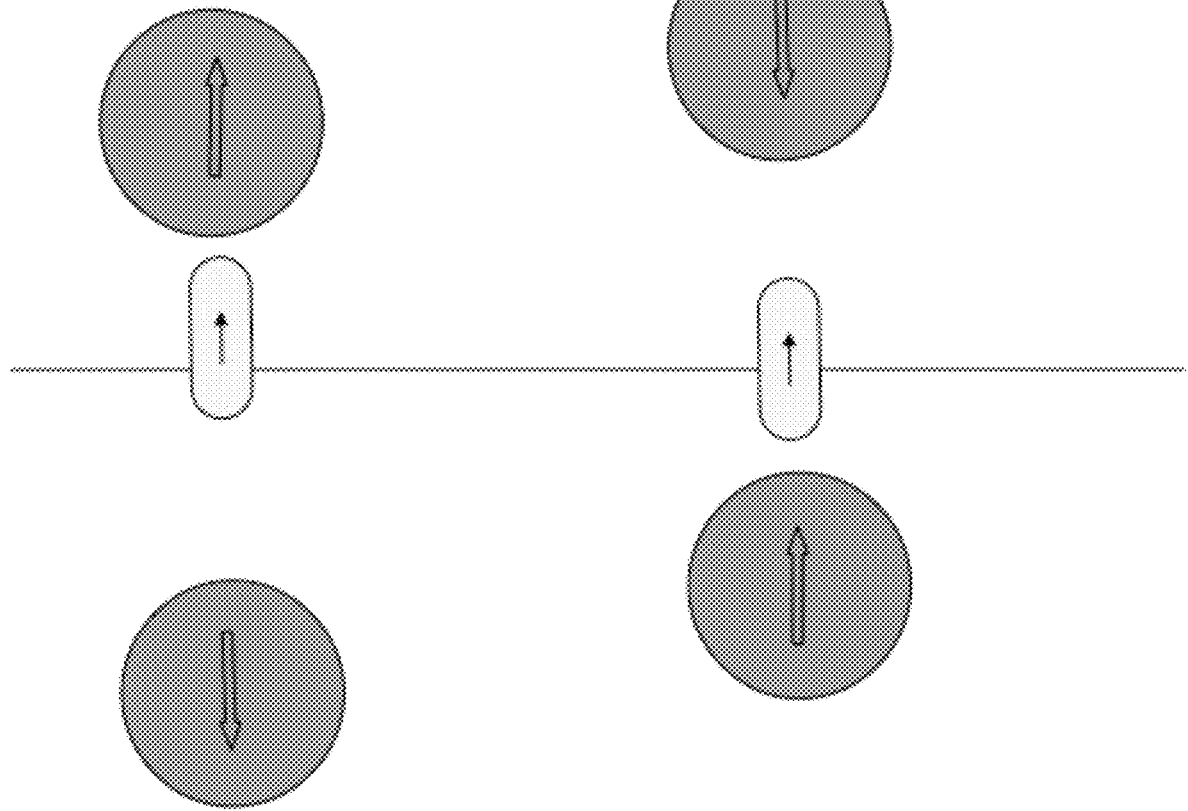
FIGS. 27 and 28 show side views of a schematic diagram to illustrate how to adjust the position of the magnetic balls to move the magnetic capsule vertically.

When the patient is under examination, in one embodiment of the same embodiment the magnetic dipole direction of the first and second magnetic field generation means are parallel to each other (FIGS. 13-14). In one example, NS direction of the first and second magnetic field generation means are parallel to each other but opposite to the magnetic dipole direction of the magnetic capsule when the patient is under examination.

Figure 10:
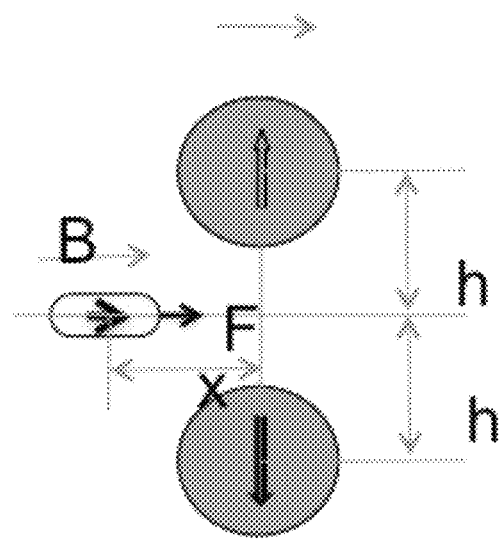
FIG. 10 is a schematic diagram to illustrate that capsule can move horizontally along an xy plane, wherein the capsule magnetization direction is the same as the forward movement direction.
Figure 11:
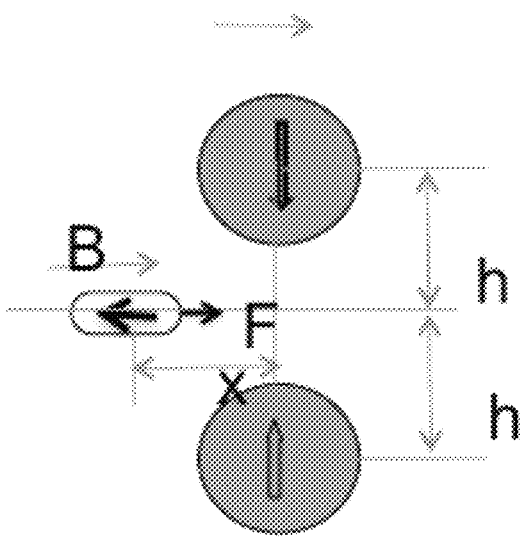
FIG. 11 is a schematic diagram to illustrate that a capsule can move vertically away from the xy plane in the z direction, wherein the capsule magnetization direction is the opposite to the forward movement direction.
Figure 12:
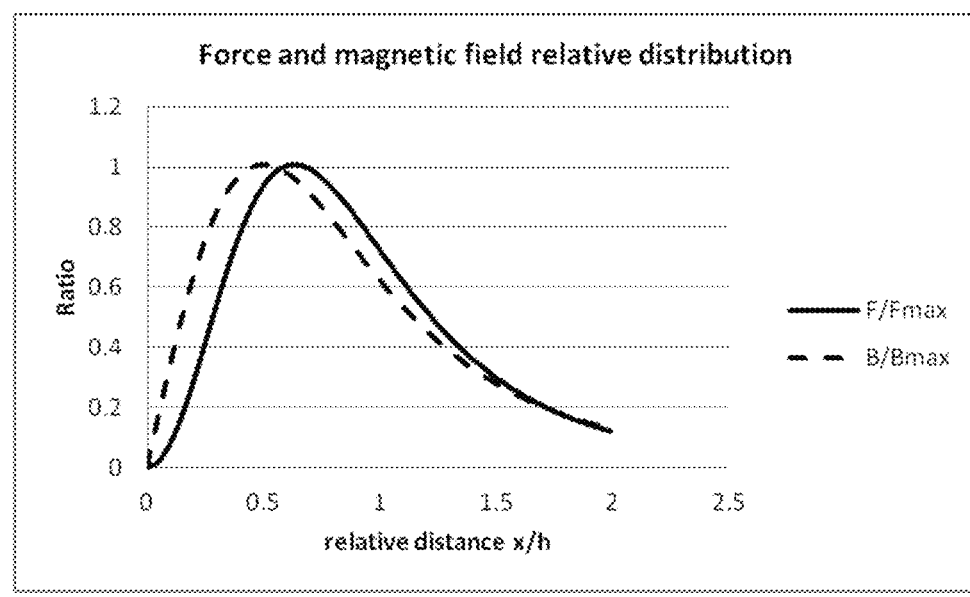
FIG. 12 is a force and magnetic field relative distribution chart when the positions of the two magnets and magnetic capsule are as listed in FIG. 11.

In another embodiment, he two magnetic dipole directions of the first and second magnetic field generation means are perpendicular to the magnetic dipole direction of the magnetic capsule (FIGS. 10 and 11). In one example, NS direction of the first and second magnetic field generation means are parallel to each other but opposite to the magnetic dipole direction of the magnetic capsule when the patient is under examination.

Bed

The system further comprises a supporting platform and the patient lies on the platform during examination. The height of the supporting platform from ground is adjustable.

The position of the supporting platform along x direction, in the z direction defines a center line of the system, because the two magnetic balls are intended to provide combined magnetic fields centered around the patient and the magnetic capsule there within. The center line may be the same as the proposed travel pathway of the magnetic capsule. In one example, the first and second magnetic field generation means are mirror images to each other across the center line. In a preferred example, the magnetic centers of the first and second magnetic field generation means are mirror images to each other, in other words they are in the same x direction.

Figure 3:
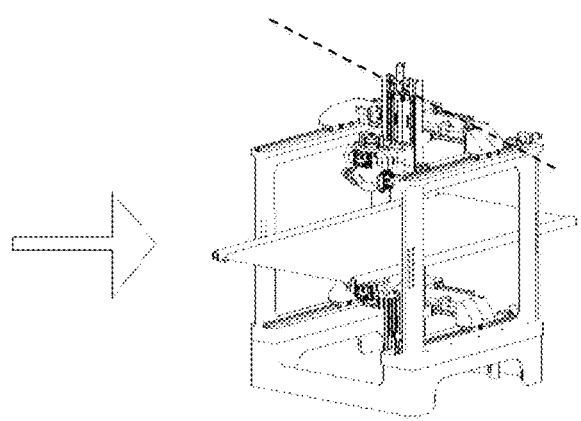
FIG. 3 shows a perspective view of the exemplar system in accordance with aspects of the present invention, wherein the bed is placed inside of the supporting frames.
Figure 4:
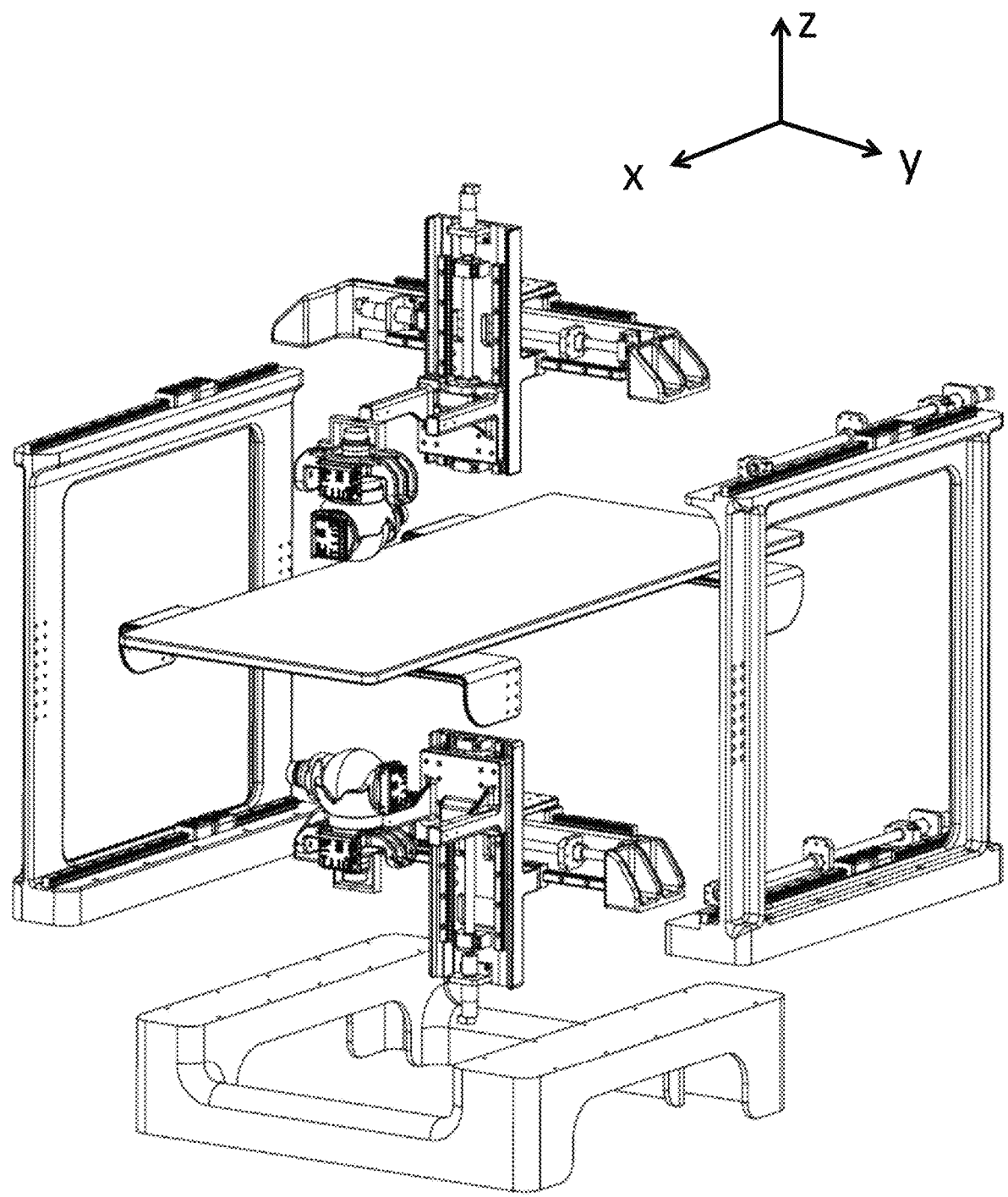
FIG. 4 shows an exploded perspective view of the exemplar system in accordance with aspects of the present invention, wherein the bed is placed inside of the supporting frames and assemblies are not placed together to better illustrate the system structure.

Referring to FIGS. 3 and 4, the platform can move in the y direction in and out from the examination area.

Mechanical Parts of the Assembly

Base

The present invention discloses a medical apparatus, comprising a base, situated on the ground. Referring to FIGS. 3 and 4, the base is square or rectangular shaped, with two of the supporting members raised above the ground and two of supporting members laid on the ground. The two members raised above the ground further comprise a top area as a supporting surface for the vertical supporting frame assemblies.

A Pair of Supporting Frame Assemblies

The medical apparatus further comprises a pair of vertical supporting frame assembly, a left vertical supporting frame assembly and a right vertical supporting frame assembly. The pair of the arranged crosswise to each other, each vertical supporting frame assembly comprising a first horizontal member and a second horizontal member, a first vertical member and a second vertical member, the second horizontal member is connected to the base on the ground. The base has a width, which is the distance between the two members that provides a top seating surface, and is also the length of two members which sit on the ground.

In each vertical supporting frame assembly, the first horizontal member is an upper horizontal member and the second horizontal member is a seating horizontal member. The seating horizontal member rests on the top supporting surface of the base.

Figure 2:
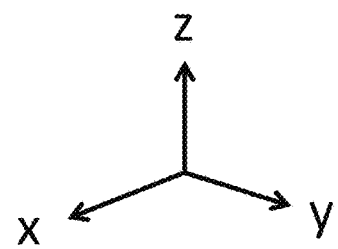
FIG. 2 shows a perspective view of an exemplar external magnetic control system in accordance with aspects of the present invention, wherein a bed is extended outside of supporting frames.
Figure 2:
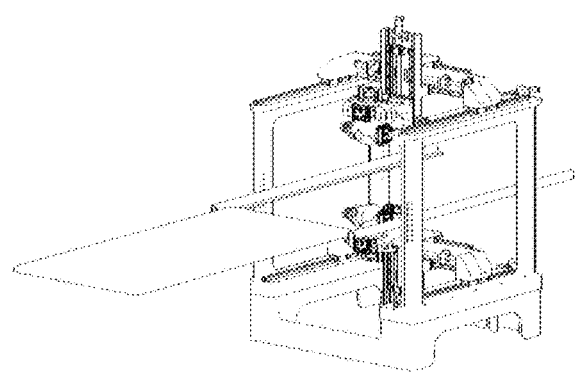

Referring to FIGS. 2-4, there are holes are at pre-determined positions of the both the first and second vertical member, configured to allow the bed to be place at different height from the ground for different patient.

Referring to FIGS. 2-3, the first vertical member of each supporting frame assembly is a front vertical member, and the second vertical member of each supporting frame assembly is a back vertical member.

Further, both the upper horizontal members and the lower horizontal members are fixed with sliding rails, which allows x-axis assemblies to travel between the front vertical member to the back vertical member and stop anywhere in between.

In one embodiment of the present invention, the medical apparatus comprises two external magnetic control systems. The two magnetic external magnetic control systems are positioned above and below the bed of the medical apparatus. The external magnetic control system positioned above the bed comprises an upper magnetic ball and upper magnetic control assembly. The external magnetic control system positioned below the bed comprises a lower magnetic ball and a lower magnetic control assembly. Referring to FIGS. 3 and 4, the upper magnetic control assembly crosses over the bed and is mounted on two opposing upper horizontal members of the pair of vertical supporting frames. The lower magnetic control assembly crosses over an open area or hollow bottom of the base and to be placed on two opposing lower horizontal members or seating members of the pair of vertical supporting frames.

x-Axis Movement Assembly

Figure 5:
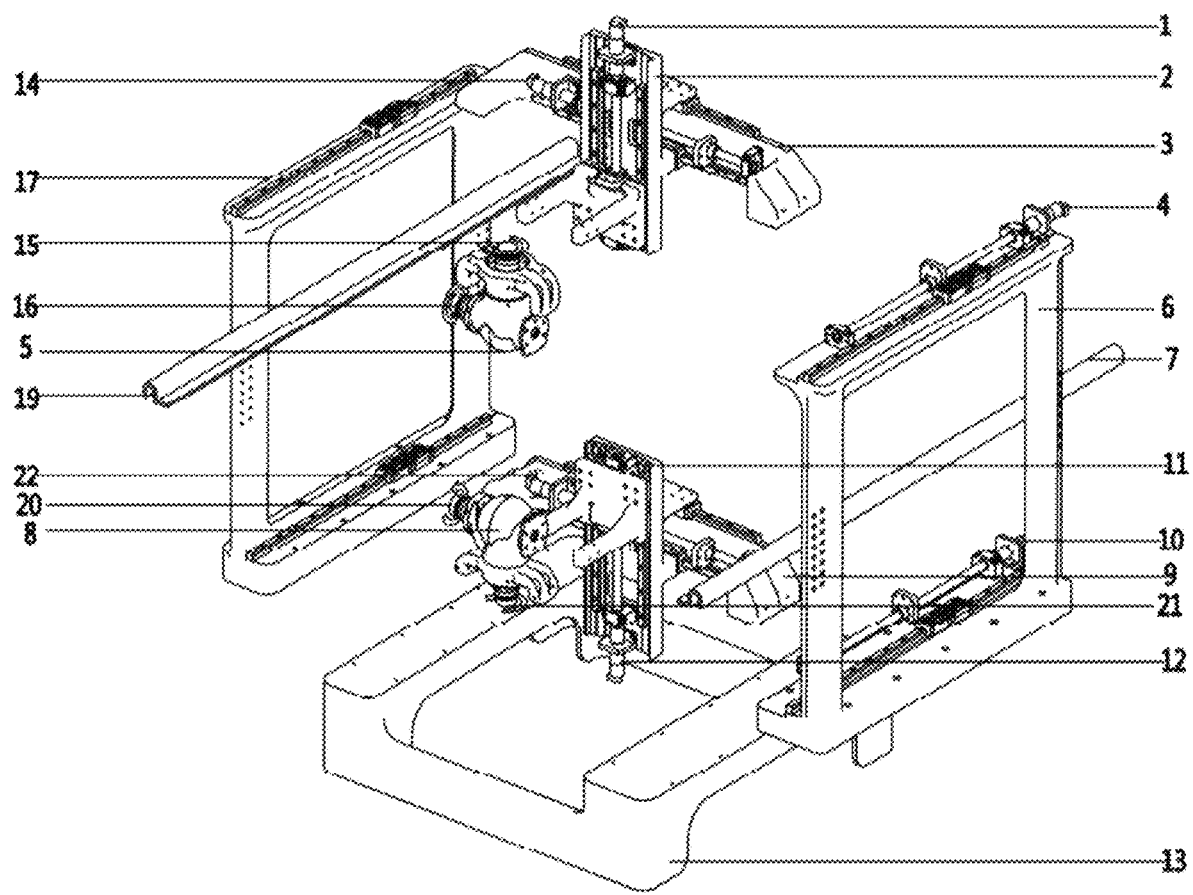
FIG. 5 shows an exploded perspective view of the exemplar system in accordance with aspects of the present invention, wherein the platform or bed is removed so that the structural components can be clearly displayed and labeled.
Figure 6:
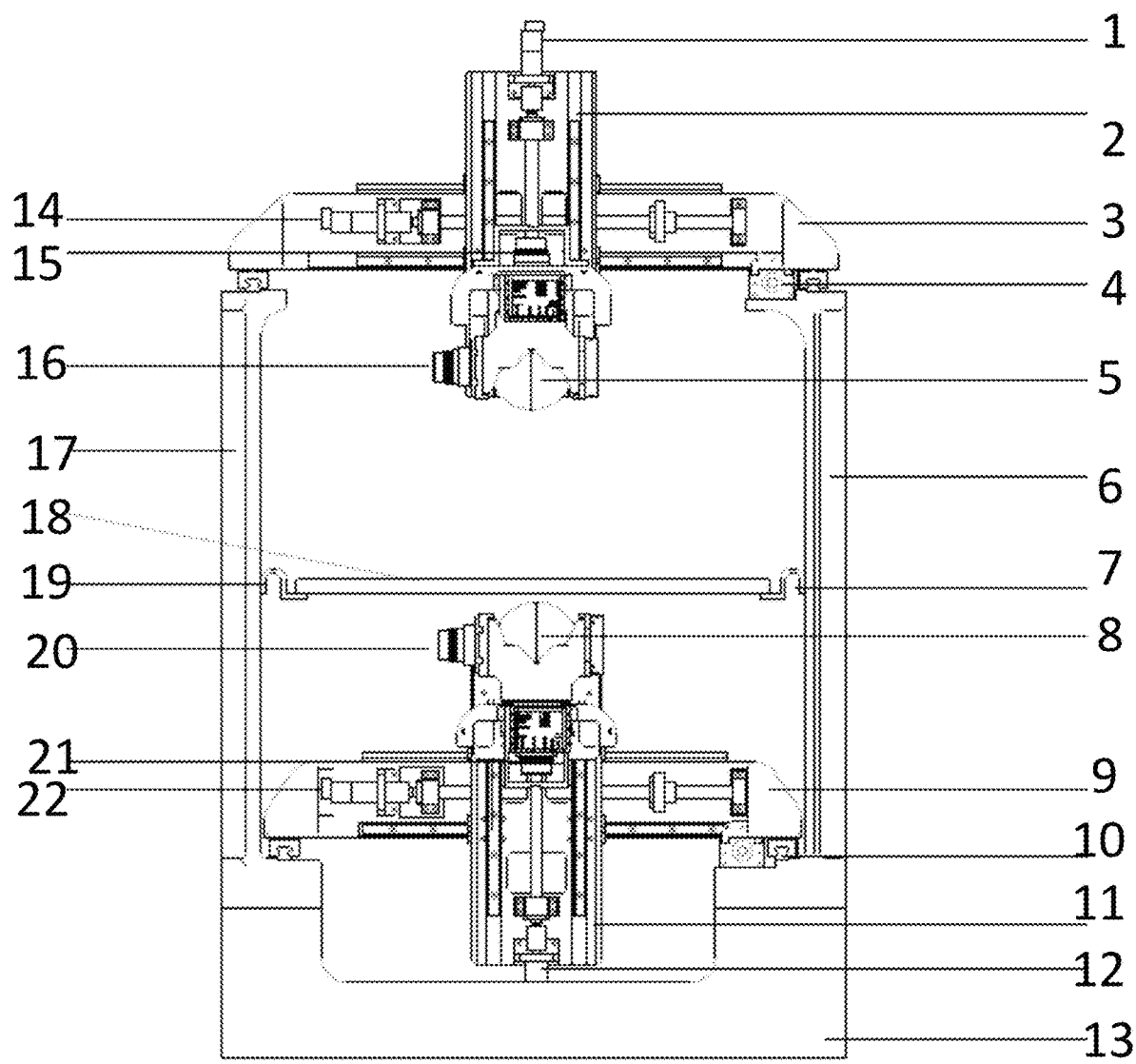
FIG. 6 is a cross sectional view of the external magnetic control system, when viewing from a back of the external magnetic control system.
Figure 7:
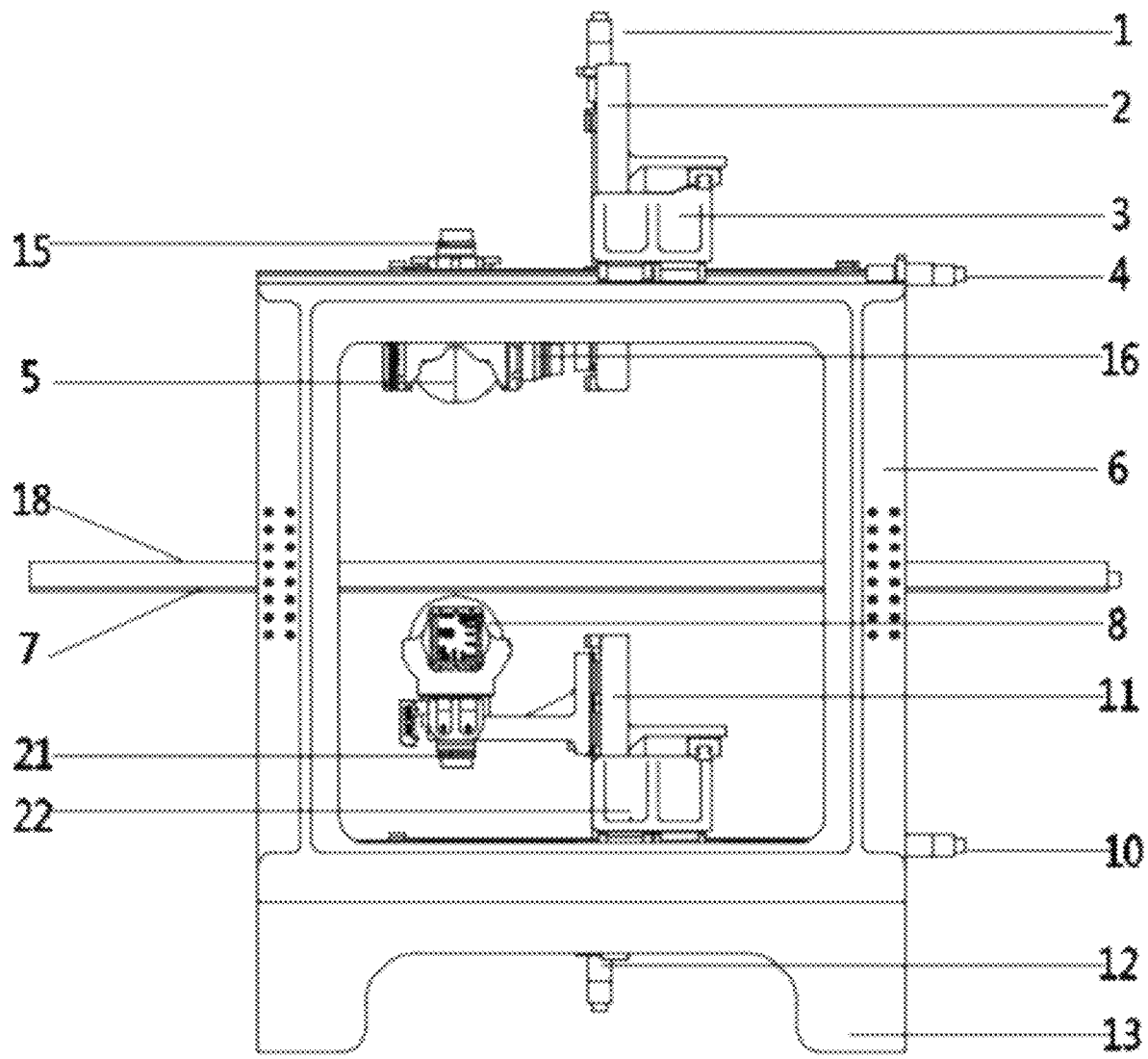
FIG. 7 is a left side view of the external magnetic control system illustrated in FIG. 6.
Figure 8:
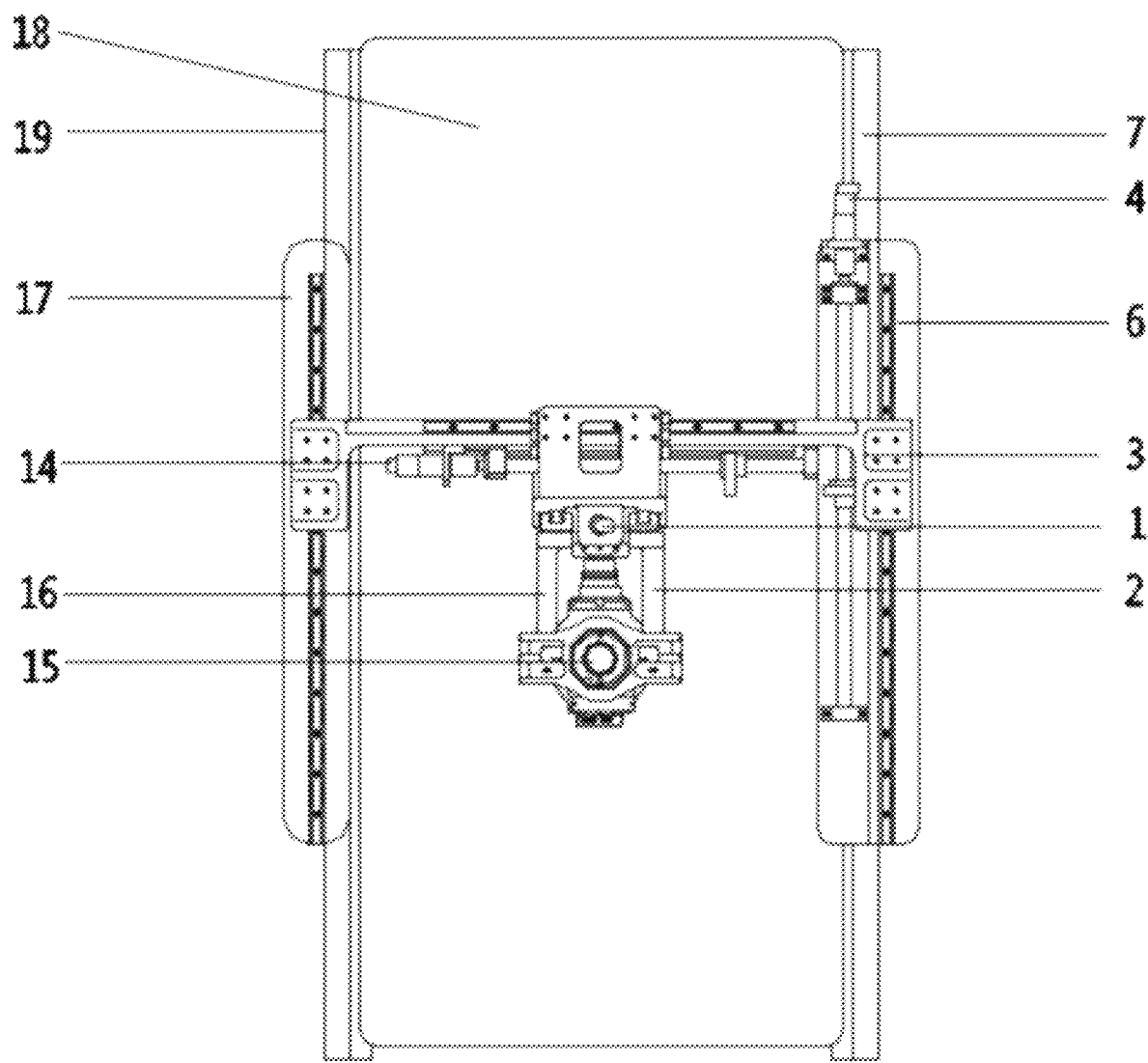
FIG. 8 is a top view of the external magnetic control system illustrated in FIG. 6.

Referring to FIGS. 3-5, a horizontal arm of the x-axis movement control assembly is mounted on the opposing horizontal members of the two vertical supporting assemblies. The movement control assembly can move between the distance from the front vertical member to the back vertical member of the vertical supporting assembly, and the magnetic balls travels within the same distance in the x direction. In one example, the x axis movement assembly can move between 0-50 cm.

y-Axis Movement Assembly

Further, the arm of the horizontal arm of the x-axis movement control assembly comprises a sliding rail in the y direction. The sliding rail is positioned on either front surface or back surface of the horizontal arm of the x-axis movement control assembly. The y axis movement control assembly is mounted onto the arm of the sliding track, is moved between the upper horizontal member of the left vertical supporting assembly and the upper horizontal member of the right vertical supporting assembly, and when the y axis movement control assembly moves, the external magnetic ball move with it. In one example, the y axis movement assembly can move between 0-30 cm.

z-Axis Movement Assembly

Additionally, y-axis movement assembly further comprises a vertical arm, perpendicular to the arm of the horizontal arm of the x-axis movement control assembly, attached to the horizontal arm of the x-axis movement control assembly through the sliding rails on the horizontal arm of the x-axis movement control assembly. The vertical arm provides a pair of sliding rails near its left edge and right edge, so that z-axis assembly can move along the pair of sliding rails up and down to move the magnetic ball away or bring it closer to the patient. The vertical arm has a bottom edge, and the bottom edge of the vertical arm is at least 5 cm away from the surface of the bed. The top edge of the vertical arm is about 20 cm-30 cm from the bottom edge of the vertical arm. The z axis assembly moves between the top edge and bottom edge of the vertical member in order to adjust the vertical position of the magnetic ball. In one example, the z-axis movement assembly can move between 0-20 cm.

Horizontal Rotation/Spin

One x-axis lever extends away from the vertical arm, attached to a first layer helmet-like cover. The first layer helmet-like cover is centered around a z-axis rotation arm, hanging down from the x-axis lever. The first layer helmet-like cover extends downwardly, leaving the magnetic ball un-covered substantially. The z-axis rotation arm brings rotation when the corresponding motor bring rotation close wise or counter clock wise along xy plane, to the magnetic ball. The first layer helmet-like cover of the horizontal rotation assembly comprises two ears.

Vertical Rotation

A second layer helmet-like cover is placed under the first layer of helmet-like cover. The second layer helmet-like cover overspread less than 50% of the surface the magnetic ball. A motor and an x-axis rotation axis are positioned on the front to back or left to right sides of the magnetic ball. The a-axis rotation axis and the corresponding motor provide rotation power to the magnetic ball, so that it can rotate around x axis and along yz plane.

In another aspect of the present invention, a method to examine a patient's GI tract using the external magnetic control system described above, is disclosed. The method comprises preparing a patient laying down on the examination bed, when capsule is inside the patient; and aligning two magnetic balls vertically and moving two magnetic balls simultaneously in a xy plane.

In one embodiment of this aspect of the present invention, the method further comprises arranging the two magnetic balls so that both have horizontal magnetization directions. In one example, the horizontal magnetization direction of the two magnetic balls are the same. In one example, the horizontal magnetization direction of the two magnetic balls are the opposite to each other.

In another embodiment of this aspect of the present invention, the method further comprises positioning the two magnetic balls so that a distance between the centers of the two magnetic balls are more than a desired vertical distance in the z direction. In one example, the desired vertical distance is more than 15 cm. In another example, the desired vertical distance is more than 30 cm. In still another example, vertical distance is more than 40 cm.

Once the examination procedure is started, the location of the capsule under the combined external magnetic field is detected through sensors in the magnetic capsule.

The method further comprises measuring the resulting combined magnetic field by magnetic sensors inside the capsules; and calculating a position and orientation of the magnetic capsule by two three dimensional magnetic sensors and one three dimensional acceleration sensor inside the capsule.

After determining the position and orientation of the magnetic capsule, the method of using further comprises adjusting the vertical and horizontal position of the two magnetic balls so that the capsule is in a middle position of two balls; moving the two magnetic balls to adjust their magnetic directions so that the magnetic capsule can image an open space of colon; and moving the two magnetic balls to be ahead of the capsule's moving direction; and moving the magnetic capsule forward by rotating the two magnetic balls to change their magnetization direction.

In one example of the present invention, the method of using including a step of dragging the magnetic capsule backwardly, the method comprising providing two magnetic balls, aligned in a vertical direction;

providing both magnetization directions of the magnetic balls parallel to each other;

providing the NS magnetization direction of the two magnetic balls opposite to each other, wherein the upper magnetic ball has the NS magnetization direction pointing down and the lower magnetic ball has the NS magnetization direction pointing up; and moving the magnetic capsule backwardly.

In another example of the present invention, the method further comprises moving the two magnetic balls close to each other at a same pace till about 5 cm-10 cm away from the surface of the patient's body.

In another example of the present invention, the method further comprises moving the magnetic capsule toward a center line (imaginary line equidistant and in—between the magnetic balls) between the centers of the upper and lower magnetic ball.

In another example of the present invention, the method further comprises adjusting a tilt angle of the magnetic capsule endoscope when the tilt angle is between 45-135 degrees.

In another example of the present invention, the method further comprises horizontally rotating the two magnetic balls together to adjust the posture or orientation of the magnetic capsule so that the two magnetization directions of the magnetic balls are perpendicular to each other.

In another example of the present invention, the method further comprises vertically rotating of the two magnetic balls together to adjust the posture or orientation of the magnetic capsule.

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. Further, when a particular feature, structure, or characteristic is described in connection with any embodiment, it is submitted that it is within the purview of one skilled in the art to affect such feature, structure, or characteristic in connection with other ones of the embodiments. Furthermore, for ease of understanding, certain procedures may have been delineated as separate procedures; however, these separately delineated procedures should not be construed as necessarily order dependent in their performance. That is, some procedures can be performed in an alternative ordering, simultaneously, etc. In addition, exemplary diagrams illustrate various methods in accordance with embodiments of the present disclosure. Such exemplary method embodiments are described herein using and can be applied to corresponding apparatus embodiments; however, the method embodiments are not intended to be limited thereby.

Although few embodiments of the present invention have been illustrated and described, it would be appreciated by those skilled in the art that changes may be made in these embodiments without departing from the principles and spirit of the invention. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein. As used in this disclosure, the term "preferably" is non-exclusive and means "preferably, but not limited to." Terms in the claims should be given their broadest interpretation consistent with the general inventive concept as set forth in this description. For example, the terms "coupled" and "connect" (and derivations thereof) are used to connote both direct and indirect connections/couplings. As another example, "having" and "including", derivatives thereof and similar transitional terms or phrases are used synonymously with "comprising" (i.e., all are considered "open ended" terms)—only the phrases "consisting of" and "consisting essentially of" should be considered as "close ended". Claims are not intended to be interpreted under 112 sixth paragraph unless the phrase "means for" and an associated function appear in a claim and the claim fails to recite sufficient structure to perform such function.

The invention claimed is:

1. A method for controlling movement of a magnetic capsule in a human GI tract, wherein said method comprises:

preparing a patient laying down on the examination bed, when capsule is inside the patient;

aligning two magnetic balls vertically where both have a horizontal magnetization;

positioning the two magnetic balls so that a distance between centers of the two magnetic balls is more than 50 cm in the vertical direction;

moving the two magnetic balls simultaneously in a XY plane;

measuring the resulting combined magnetic field using magnetic sensors inside the capsules;

calculating a position and orientation of the magnetic capsule by two three dimensional magnetic sensors and one three dimensional acceleration sensor inside the capsules;

adjusting the vertical and horizontal position of the two magnetic balls so that the capsule is between the two balls;

moving the two magnetic balls to adjust their magnetic directions so that the magnetic capsule can image an open space of colon; and moving the two magnetic balls to be ahead of the capsule's moving direction; and moving the magnetic capsule forward by rotating the two magnetic balls to change their magnetization direction.

2. The method of claim 1, further comprising moving the capsule backward and rotate the two magnetic balls so that magnetic direction of the two magnetic balls are perpendicular to the magnetic direction of the magnetic capsule, while the magnetic direction of both the two magnetic balls pointing to a respective opposite ball of the two balls.

3. The method of claim 1, further comprising moving the two magnetic balls close to each other at the same pace to 5 cm-10 cm from the surface of the patient's body.

4. The method of claim 1, further comprising moving capsules toward an imaginary line equidistant and in-between the magnetic balls.

5. The method of claim 1, further comprising adjusting a tilt angle of the magnetic capsule endoscope when the tilt angle is between 45-135 degrees, wherein the tilt angle is an angle formed between the magnetization direction of the capsule and an imaginary line equidistant and in-between the magnetic balls.

6. The method of claim 1, further comprising horizontally rotating the two magnetic ball together to adjust the orientation of the magnetic capsule.

7. The method of claim 1, further comprising vertically spinning the two magnetic balls together to adjust the orientation of the magnetic capsule.

* * * * *